(12) United States Patent
Jahn et al.

(10) Patent No.: US 6,443,984 B1
(45) Date of Patent: Sep. 3, 2002

(54) ADJUSTABLE INTRAOCULAR LENS AND METHOD FOR ITS PRODUCTION

(76) Inventors: Marianne Jahn; Claus-Ekkehard Jahn, both of Kempten (DE)

( * ) Notice: Subject to any disclaimer, the term of this patent is extended or adjusted under 35 U.S.C. 154(b) by 0 days.

(21) Appl. No.: 09/631,727

(22) Filed: Aug. 3, 2000

(30) Foreign Application Priority Data

Aug. 4, 1999 (DE) .......................................... 199 36 666

(51) Int. Cl.$^7$ ................................................ A61F 2/16
(52) U.S. Cl. ..................................... 623/6.22; 623/6.43
(58) Field of Search ............................... 623/6.11, 6.22, 623/6.38, 6.43, 6.39, 6.42, 6.46

(56) References Cited

U.S. PATENT DOCUMENTS

| | | |
|---|---|---|
| 4,753,655 A | 6/1988 | Hecht |
| 4,787,903 A | 11/1988 | Grendahl |
| 4,863,465 A | 9/1989 | Kelman |
| 5,288,293 A | 2/1994 | O'Donnell, Jr. |
| 5,326,347 A | 7/1994 | Cumming |
| 5,567,365 A | 10/1996 | Weinschenk, III et al. |
| 5,571,177 A | 11/1996 | Deacon et al. |
| 5,593,437 A | 1/1997 | Arita et al. |
| 5,766,244 A | 6/1998 | Binder |
| 5,800,533 A * | 9/1998 | Eggleston et al. ......... 623/6.39 |
| 6,013,101 A * | 1/2000 | Israel ........................ 623/6.43 |

* cited by examiner

Primary Examiner—Dinh X. Nguyen
(74) Attorney, Agent, or Firm—Breiner & Breiner, L.L.C.

(57) ABSTRACT

The invention relates to an adjustable intraocular lens with a lens body 1, haptic arms 3 for fixing the lens body 1 in the eye, and an adjustment means for moving the lens body 1 relative to the haptic arm 3 in the direction of the optic axis 27 of the lens body 1 and for adjusting the extent of the movement. The haptic arms 3 are each directly connected to the lens body 1 via one of their ends. The haptic arms 3 preferably have a bifurcation 31, 33, and only one of the two fork ends 31 is connected to the lens body 1. The adjustment means, preferably with an adjusting screw 37, is screwed through one of the two fork ends 31, 33, and changes the distance between the two fork ends 31, 33. The intraocular lens according to the invention is easy and inexpensive to produce.

15 Claims, 5 Drawing Sheets

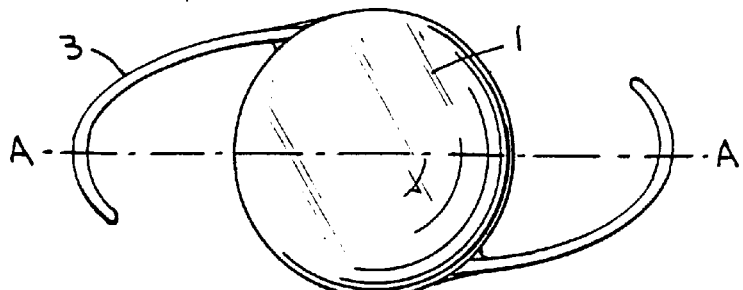
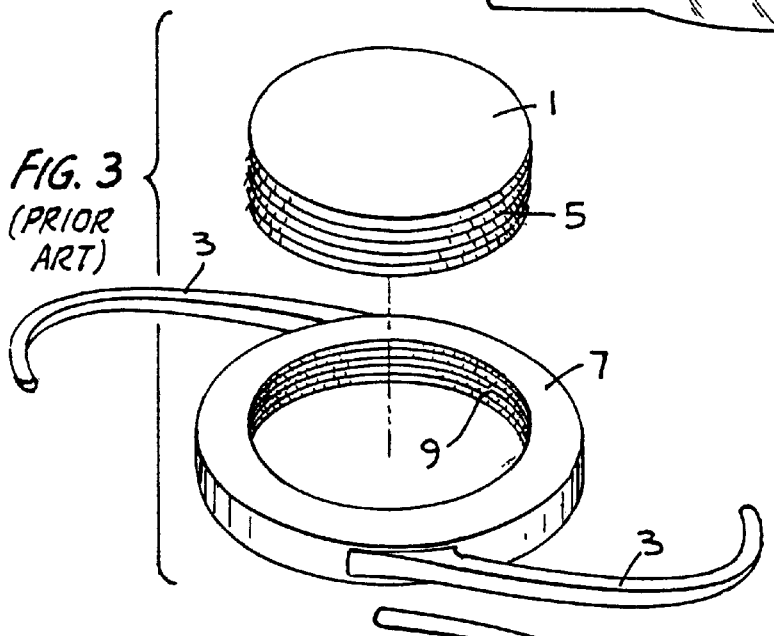
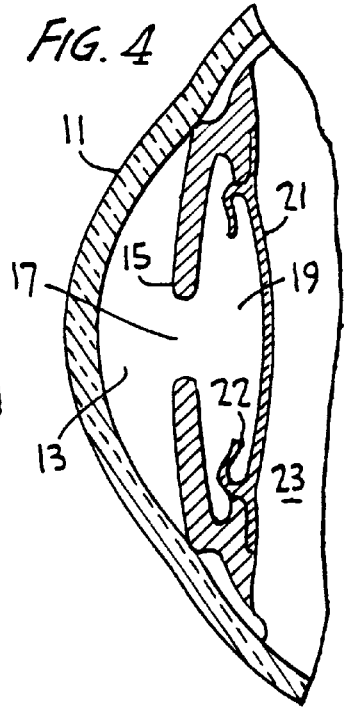
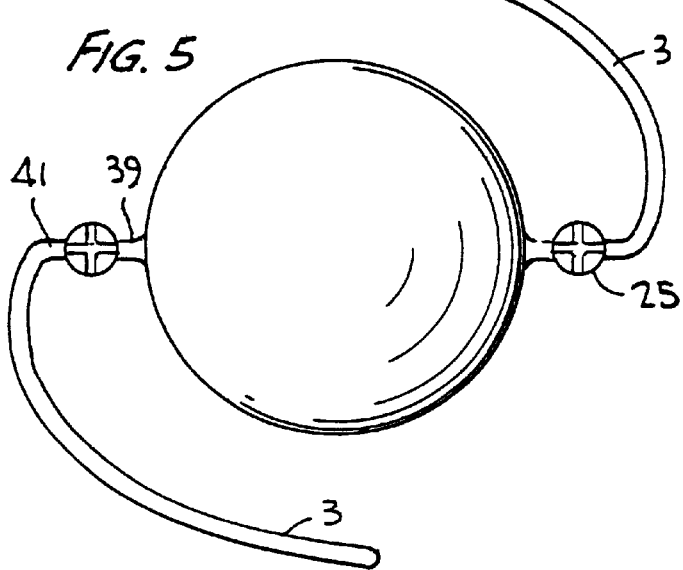

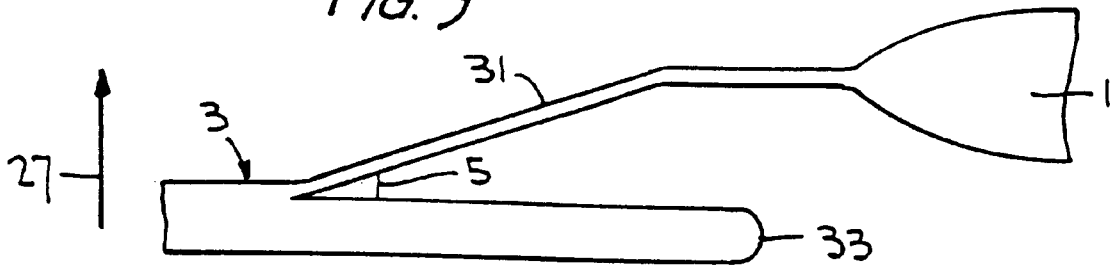
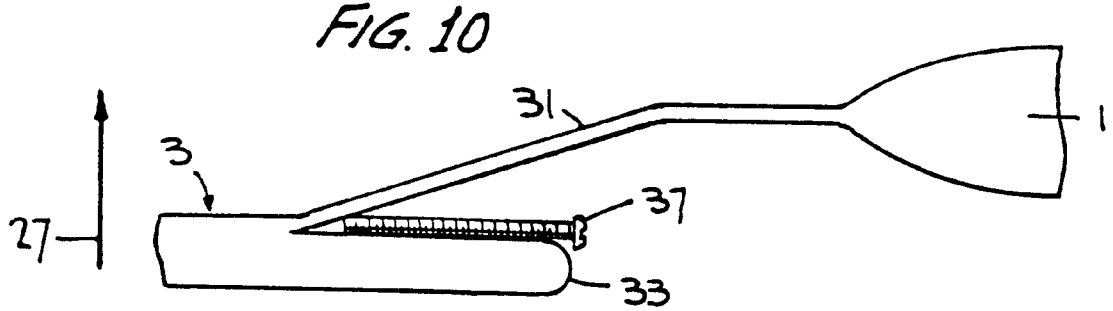
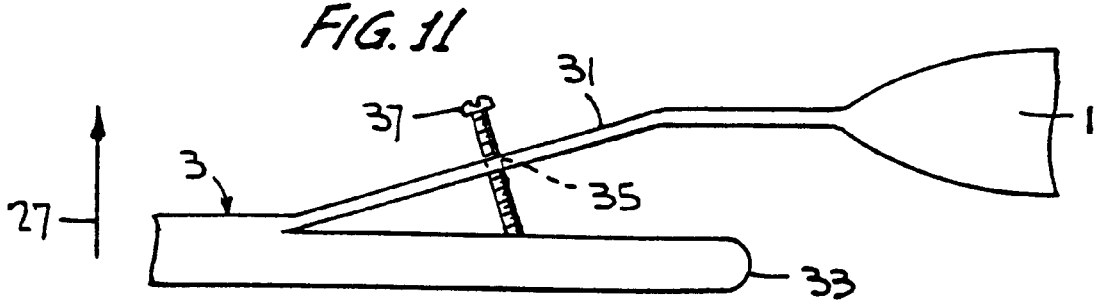
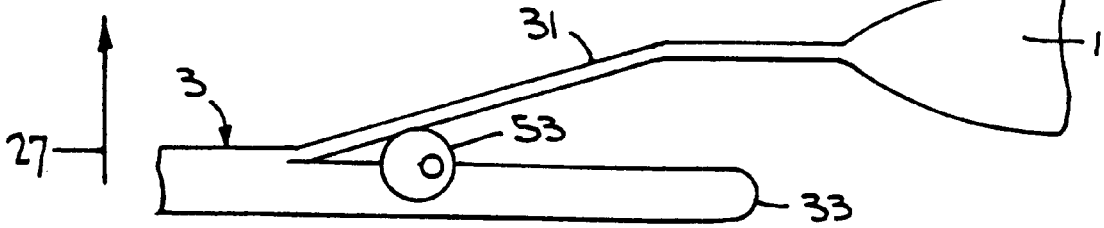

ADJUSTABLE INTRAOCULAR LENS AND METHOD FOR ITS PRODUCTION

TECHNICAL FIELD

The invention relates to an intraocular lens and in particular to an intraocular lens in which the focus can be adjusted after implantation. The invention also relates to a method for production of such a lens.

PRIOR ART

In patients affected by grey cataract, for example, it is at present customary to remove the diseased and opaque crystalline lens and to replace it with an implant, a so-called intraocular lens (IOL).

An example of an intraocular lens of this type is shown in FIGS. 1 and 2. The lens consists of a lens body 1 and of two haptic arms 3 connected to the lens body 1. FIG. 2 shows a side view of the lens from FIG. 1.

The lens is preferably made of a soft or foldable material so that it can be folded or rolled along the broken line (A—A). For implantation, after the diseased crystalline lens has been removed, the intraocular lens is inserted into the eye by being folded together during the insertion along the broken line so that the incision in the cornea can be made as small as possible. The lens is unfolded within the eye and is secured in its position, usually in the capsule of the removed lens.

The lenses, which are usually made of a synthetic material such as polyurethane elastomer, silicone elastomer, hydrogel polymer or collagen, can be formed in one piece and are therefore economical to produce. As they can be rolled up or folded up, they can be inserted through a small slit, with the result that the eye rapidly heals after the operation.

However, a disadvantage of these lenses is that incorrect fitting can easily occur, with the result that, even after the operation, the patient requires a means for correcting vision, for example glasses or contact lenses, because the focus of the lens lies before or behind the retina.

To rectify this problem, an adjustable intraocular lens has been proposed in U.S. Pat. No. 5,800,533 and in U.S. Pat. No. 5,728,155. Such a lens is shown in FIG. 3. This prior art lens consists of a cylindrical lens body 1 with an external thread 5, a support device 7 which is annular and has an internal thread 9 matching the external thread 5 of the lens body 1, and haptic arms 3 which are secured to the support device or are formed in one piece with the latter. As the lens body is screwed to a greater or lesser extent into the support device, the distance between the lens body and the retina, and thus the focus, is adjusted.

U.S. Pat. No. 5,728,155 also shows that a flexible lens body can be fitted into the support device, so that it is possible subsequently to exchange the lens via a small incision made through the cornea. This publication additionally discloses that the lens body can also be moved relative to the support device by means other than an internal thread and an external thread. For example, the lens can be moved using a worm gear secured on the support device.

However, these adjustable intraocular lenses have a number of disadvantages. On the one hand, they are difficult to produce because they are made up of several parts which have to fit each other with very tight tolerances. In particular, movement mechanisms using worm gears and the like are elaborate, complicated and expensive to produce.

A further disadvantage is that the lens body is held in an annular support device. The latter is usually rigid, so that a large incision is needed for implantation. Moreover, the support device reaches close to the field of vision of the patient, with the result that undesired reflexes and disturbances can be caused by the thick support device.

Further adjustable intraocular lenses are known from U.S. Pat. No. 5,203,788 and from U.S. Pat. No. 5,288,293. In particular, U.S. Pat. No. 5,288,293 discloses an intraocular lens in which the angle between the haptic arms and the lens body can be adjusted by an adjustment means, so that the lens body can be moved relative to the haptic arms in the direction of the optic axis. The adjustment means is a material formed at the juncture between the haptic and which connect to the implant lens. This material may be more readily subjectable to hydration, or in other cases to dehydration, such as the type of hydrogel or colagene. Thus, modifying the hapticoptic angle through laser energy treatment provides for an effect in the change of implant power. However, this kind of adjustment is not very precise and can be done only once. The adjustment is not reversible. Furthermore, the material placed at the boarder of the implant lens may cause undesired optical disturbance.

The object of the invention is to make available an adjustable intraocular lens which is easy and inexpensive to produce and which avoids the stated disadvantages.

SUMMARY OF THE INVENTION

This object is achieved by means of an adjustable intraocular lens and by means of a method for its production.

According to a further advantageous aspect of the invention, the whole lens can be folded or rolled so that it can be inserted through a small incision in the cornea.

In a particularly advantageous embodiment, the lens body and the haptic arms are made in one piece in one casting procedure.

According to a further advantageous embodiment of the invention, the adjustment means is a commercially available screw which can be re-adjusted after implantation, either by means of a very small incision through the cornea and engagement of an instrument in the screw, or non-invasively using a magnetic screwdriver.

A further aspect of the invention provides for the lens being adjusted by means of an electric motor, for example a piezoelectric element.

An advantage of the invention lies in the provision of an adjustable intraocular lens having an adjustment mechanism which does not cause optical disturbance.

A further advantage of the present invention lies in the fact that the adjustable intraocular lens can be adjusted repeatedly and reversibly.

BRIEF DESCRIPTION OF THE DRAWINGS

The invention is now explained with reference to the attached drawings, in which:

FIG. 1 shows a plan view of a known lens which is not adjustable;

FIG. 2 shows a side view of the lens in FIG. 1;

FIG. 3 shows an adjustable lens according to the prior art;

FIG. 4 shows a transverse section through a human eye from which the crystalline lens has been removed;

FIG. 5 shows a plan view of a lens according to the invention;

FIG. 9 shows a side view of a further lens according to the invention;

FIG. 10 shows a side view of a further lens according to the invention;

FIG. 11 shows a side view of a further lens according to the invention;

FIG. 12 shows a side view of a further lens according to the invention;

DETAILED DESCRIPTION OF THE INVENTION

Figure 6A:
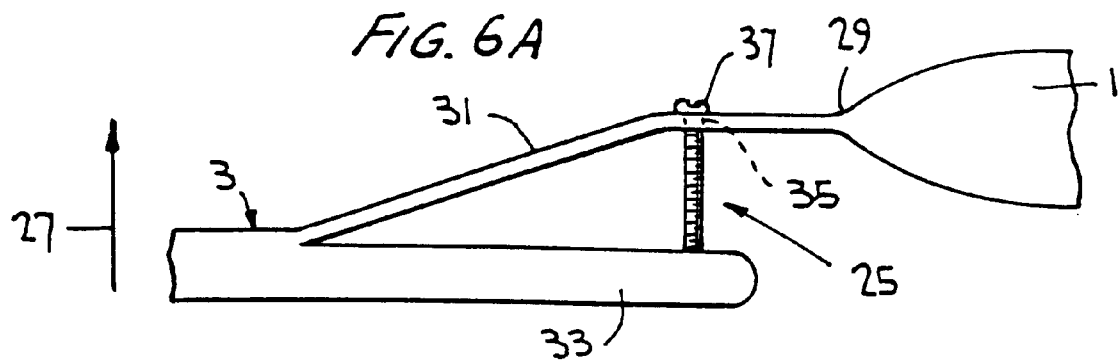
FIG. 6a shows a side view of a lens according to the invention, at maximum adjustment.

The human eye is shown in section in FIG. 4, the crystalline lens having been removed. Situated behind the cornea 11 consisting of transparent tissue is the anterior chamber 13 of the eye. This anterior chamber 13 is delimited by the iris 15 and the pupil 17. Adjoining it is the posterior chamber 19 which, for its part, is delimited on one side by the iris 15 and the pupil 17 and on the other side by the vitreous membrane 21 and the vitreous body 23. The intraocular lens is usually arranged in the posterior chamber, the haptic arms 3 bearing against the margin of the posterior chamber or against the capsule 22 and holding the lens in position.

FIG. 5 shows a plan view of a lens according to the invention. The lens comprises a lens body 1, which is adjoined by two haptic arms 3 lying opposite each other. The haptic arms 3 have adjustment means 25 for moving the lens body 1 relative to the haptic arms 3 in the direction of the optic axis 27 of the lens body 1 and for adjusting the extent of the movement.

Figure 6B:
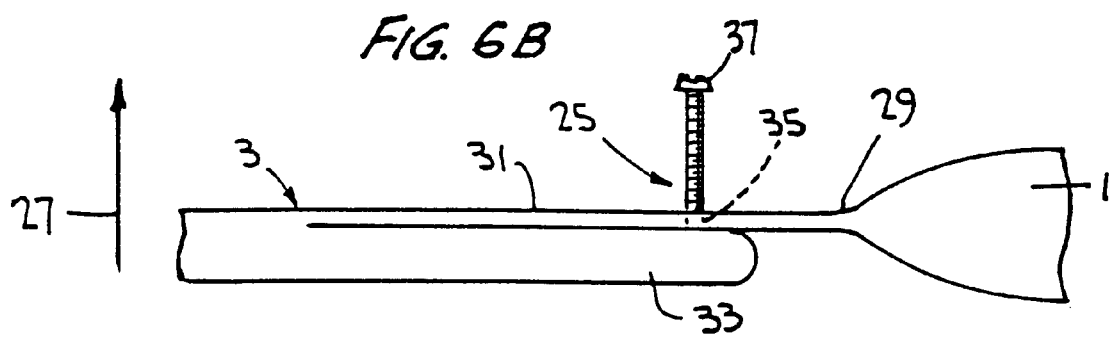
FIG. 6b shows a side view of a lens according to the invention, at minimum adjustment.

FIG. 6a shows a side view of part of a lens according to the invention, one of the haptic arms 3 with the adjustment means 25 being shown in the maximum extended position, while FIG. 6b shows the same part of the lens with the haptic arm 3 and the adjustment means 25 in the maximum drawn-in position.

At its end 29 directed towards the lens body, the haptic arm 3 has a bifurcation with two fork ends 31, 33. The fork end 31 is connected to the lens body 1. It is made flexible, at least at its connection points to the lens body 1 and to the other fork end 33, so that a relative movement of the two fork ends is possible. The whole haptic arm 3 is preferably made of a synthetic material having a certain elasticity. Moreover, the other fork end 33 is preferably stiffer than the fork end 31. This can be realized by suitable choice of material or by giving the two fork ends suitable thicknesses. In the embodiment shown, the fork end 33 is many times thicker than the fork end 31.

At its end directed towards the lens, the fork end 33 is provided with a rounded edge, so that when the lens is fitted there is no projecting part on which the lens could become hooked with the iris or cornea.

The rear part of the haptic arms 3, from which the two fork ends 31, 33 extend, can be made of a relatively soft, elastic material. The use of a material with a "memory" effect, which returns to its original shape on heating after deformation, is also possible.

In this embodiment, the fork end 31 carries the adjustment means 25. The latter consists of a threaded hole 35 extending through the fork end 31 in the direction of the optic axis 27. An adjusting screw 37 is screwed into the threaded hole 35 in such a way that its front end bears on the other fork end 33 and is pressed against it by the spring force of the elastic fork elements 31, 33.

As can be seen from FIG. 6a and FIG. 6b, the position of the lens body 1 relative to the fork end 33 changes as the adjusting screw 37 is screwed in and out. Accordingly, after inserting the adjustable intraocular lens, the ophthalmic surgeon is able to adjust the focus of the lens accurately to the retina of the patient.

To do this, the intraocular lens can first be fitted in the eye without the adjusting screw, that is to say with the fork ends 31, 33 bearing against each other. After the results of this operation have healed, the vision defect of the patient can be determined. Then, in a minor intervention performed under local anaesthesia, the cornea can be opened directly above the threaded hole 35, and adjusting screws 37 of the required length can be screwed in. To do this, only a very small corneal incision is required, which lies outside the field of vision and rapidly heals.

Alternatively, the intraocular lens can be fitted together with the inserted adjusting screw 37, in which case the adjusting screw is preferably screwed in to about half way.

By selecting a screw of suitable length, a lens adjustment of up to 5 dioptres (3.25 mm) can be achieved without problem.

The lens itself can be produced in a casting procedure, after which the bifurcation into the fork ends 31, 33 is made by cutting through the haptic arms 3. A threaded hole 35 is subsequently formed in the bifurcation 31. Alternatively, the lens can be produced together with its haptic arms 3, the bifurcation and the threaded hole 35 all in one casting procedure.

The intraocular lens according to the invention is economical to produce, uncomplicated and easy to handle and it offers the surgeon a wide range of adjustment possibilities.

Figure 7:
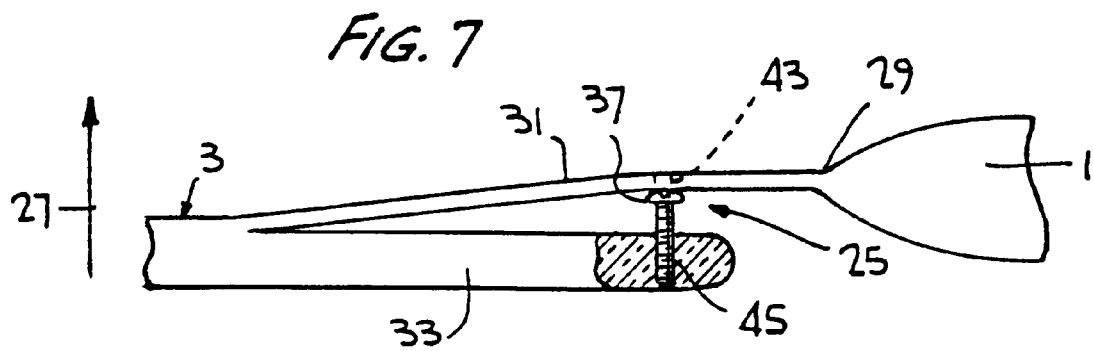
FIG. 7 shows a side view of a further lens according to the invention.

FIG. 7 shows a further embodiment of the invention. The embodiment shown in FIG. 7 differs from that in FIGS. 6a and 6b in the following respects. The adjustment means in this embodiment consists of an unthreaded through-hole 43 in the fork end 31, an adjusting screw 37, and a blind threaded hole 45 on the other fork end 33. The adjustment of the lens body 1 in this case is effected by an instrument engaging through the unthreaded through-hole 43 into the head of the adjusting screw 37, which bears from underneath on the fork end 31, that is to say in the space between, the two fork ends 31, 33. By turning the screw 37, the fork end 31 can be raised or lowered relative to the fork end 33. Since the fork end 33 of the haptic arm 3 is made substantially thicker than the fork end 31, adjustment is thus possible over a large range, without changing the screw and without projections protruding from the lens and possibly damaging the eye.

Besides the embodiments shown, there are other adjustment possibilities. For example, the screw in the embodiments in FIGS. 6a, 6b and 8 can be replaced by a piezo-electric element which forces the two fork ends 31, 33 away from each other. Alternatively, spacer elements, for example wedge-shaped spacer elements, can be pushed in between the two fork ends. It is also possible to position an elastic, fluid-filled cushion between the two fork ends and to deliver or aspirate fluid for purposes of adjustment.

The haptic arms 3 can also consist of two arm layers which are connected firmly to each other over a first section.

The soft lens body 1 can also have a solid thin outer ring which can preferably be folded via two hinges together with the lens. This outer ring can additionally carry two catch elements which, after implantation, hold the lens body in the unfolded position.

Figure 8:
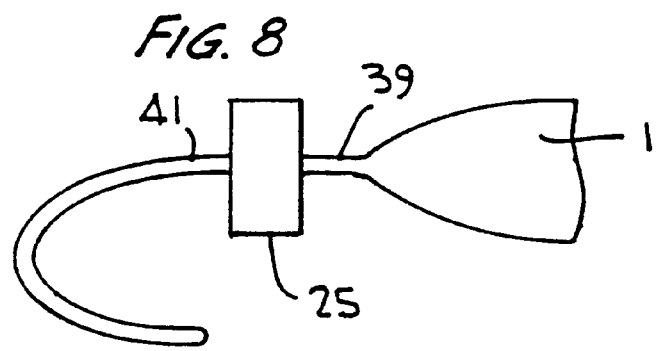
FIG. 8 shows a side view of a further lens according to the invention.

FIG. 8 shows the side view of a further lens according to the invention. In the lens shown, the haptic arms 3 are not bifurcated, and instead they have an adjustment means 25 in the form of a worm gear. The haptic arms 3 are divided in two. A first section 39 extends between the lens body 1 and the adjustment means 25. A second section 41 extends from the adjustment means 25 away from the lens. In this embodiment, the adjustment means 25 is preferably a worm gear, so that the position of the section 39 of the haptic arm 3 can be adjusted relative to the section 41 of the haptic arm 3.

This embodiment has the advantage that adjustment of the lens by 3.25 mm is possible without replacement of the screw. Since the worm gear is positioned at a distance from the lens via the section 39 of the haptic arm 3, it does not lie in the patient's field of vision and does not cause unwanted reflexes.

The worm gear can be designed such that it allows the lens body 1 together with the sections 39 of the haptic arms 3 to be replaced without the other sections 41 of the haptic arms 3 having to be replaced. In this way, it is possible, for example in children, to take account of the changes in the eye over the course of time, without major surgery being needed.

Other different embodiments of the intraocular lens according to the invention are shown in FIGS. 9 to 19.

The adjustable intraocular lens in FIG. 9 has a wedge-shaped spacer element 51 between the fork ends 31, 33, which spacer element can be moved in order to change the lens position.

Further adjustable intraocular lenses are shown in FIGS. 10 and 11. Here, the adjusting screw 37, the threaded hole 35 and the through-hole 43 are inclined relative to the optic axis 27. In this way, the point of intervention on the cornea, for post-operative adjustment, moves outwards and away from the patient's field of vision.

In the lens according to FIG. 12, an eccentric disc is provided as spacer element 53.

Figure 13:
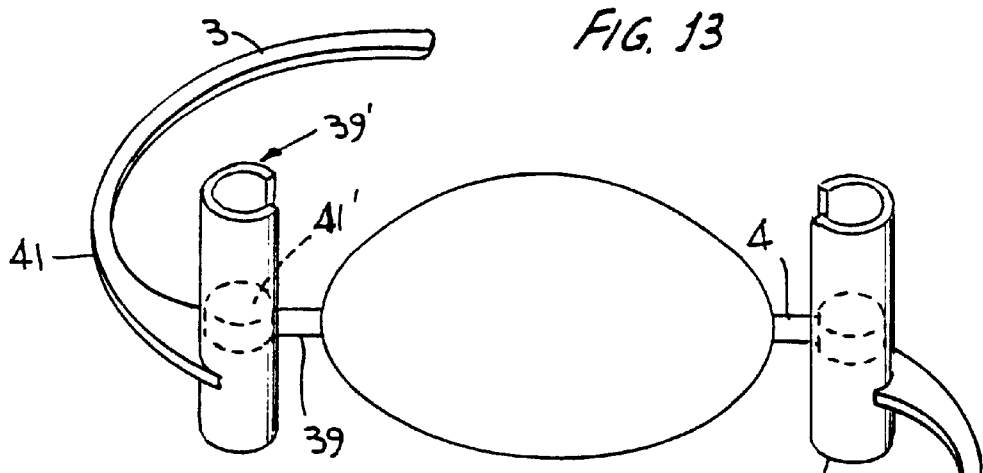
FIG. 13 shows a side view of a further lens according to the invention.

In the lens according to FIG. 13, the adjustment means is in the form of a clamp guide parallel to the optic axis 27.

In this preferred embodiment, one section 41 of the haptic arm, arranged with one end on the lens, has a cylindrical or disc-shaped end-piece 41' aligned with the optic axis 27 at the other end. The other section 39 of the haptic arm has, at one end, a hollow cylindrical or flange-like end-piece 39' which encloses the disc-shaped end-piece 41'. The section 41 of the haptic arm protrudes through a preferably continuous slot in the wall of the end-piece 39'.

The interior of the hollow cylindrical end-piece 39' and the outer contour of the disc-shaped end-piece 41' are matched to each other. The end-piece 41' can be held in the other end-piece 39' by a clamping effect, and their relative position can be mechanically adjusted.

The two end-pieces 39' and 41' together form the adjustment means. The two end-pieces 39' and 41' are preferably formed in such a way that they cannot twist relative to each other; for example, the hollow cylinder and the disc can each have oval shapes. Other forms are also possible, however, such as semicircles, polygons or "dogs'bones". In this description, the term "hollow cylinder" is therefore not to be understood as being restricted to circular cylinders. The clamping principle can also be modified such that a relatively thin flange as one end-piece comprises a longer pin than the other end-piece.

The hollow cylindrical end-piece 39' and the section 41 of the haptic arm 3 can be made in one piece from metal, whereas the disc-shaped end-piece 41' together with the lens - preferably in one piece- is made of a plastic material.

It is also preferable for the section 39 and the end-piece 39' to be ensheathed in a biocompatible plastic.

The design of the hollow cylindrical end-piece 39' of metal with a continuous longitudinal slit in the outer wall has the advantage of an elastic or resilient adaptation of the end-piece 39' to the end-piece 41' received therein.

Alternatively, the hollow cylindrical end-piece can also be formed on the section 41 of the haptic arm, that is to say on the side towards the lens body.

Figure 19:
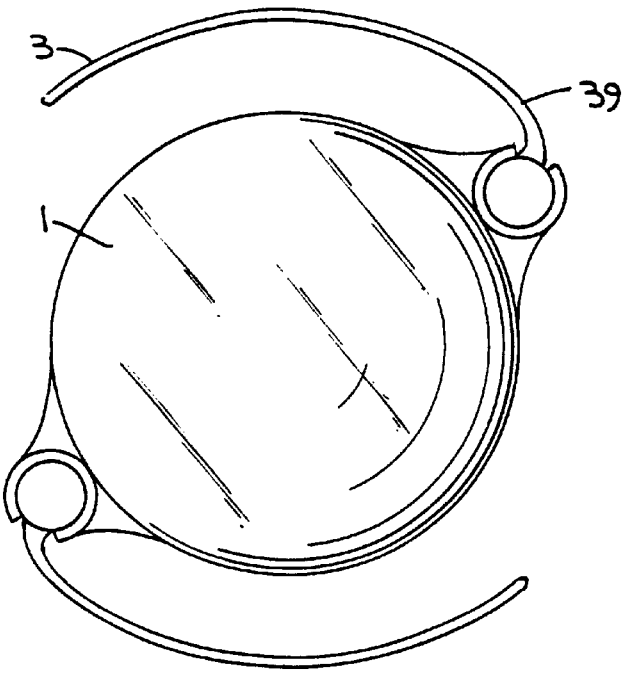
FIG. 19 shows a plan view of a further lens according to the invention.

In a presently preferred embodiment, shown in FIG. 19, a through-hole is made for this purpose in the edge of the lens body, parallel to the optic axis. A longitudinal slit permits connection to the other section 39 of the haptic arm. In other words, in this embodiment the adjustment means is formed in the edge of the lens body, and not connected to the lens body via a section 41 of the haptic arm.

Figure 14:
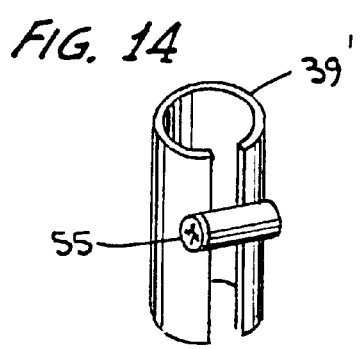
FIG. 14 shows a view of a further adjustment means.

FIG. 14 shows a further possibility in which, after positioning, the lens can be secured by an arrest means 55, for example a screw.

Figure 15:
FIG. 15 shows a side view of a further lens according to the invention.

In the adjustable intraocular lens in FIG. 15, the adjustment means 25 has a pin 47 which extends in the direction of the optic axis 27 and which is firmly connected to one of the two sections 39 of the haptic arm 3, while the other section 41 is mounted so that it can move along the pin 47.

Horseshoe-shaped spacers 53 can be pushed firmly onto the pin 47 between the two sections 39, 41 and fix the distance between the sections 39, 41.

Alternatively, as has been mentioned, the sections 39, 41 can also be held in their relative position by a clamping effect.

Figure 16:
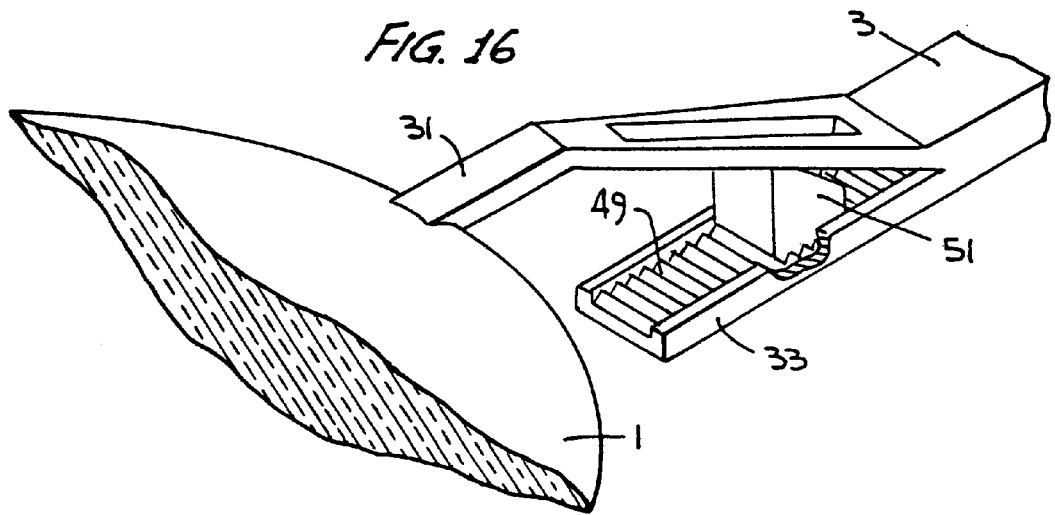
FIG. 16 shows a side view of a further lens according to the invention.
Figure 17:
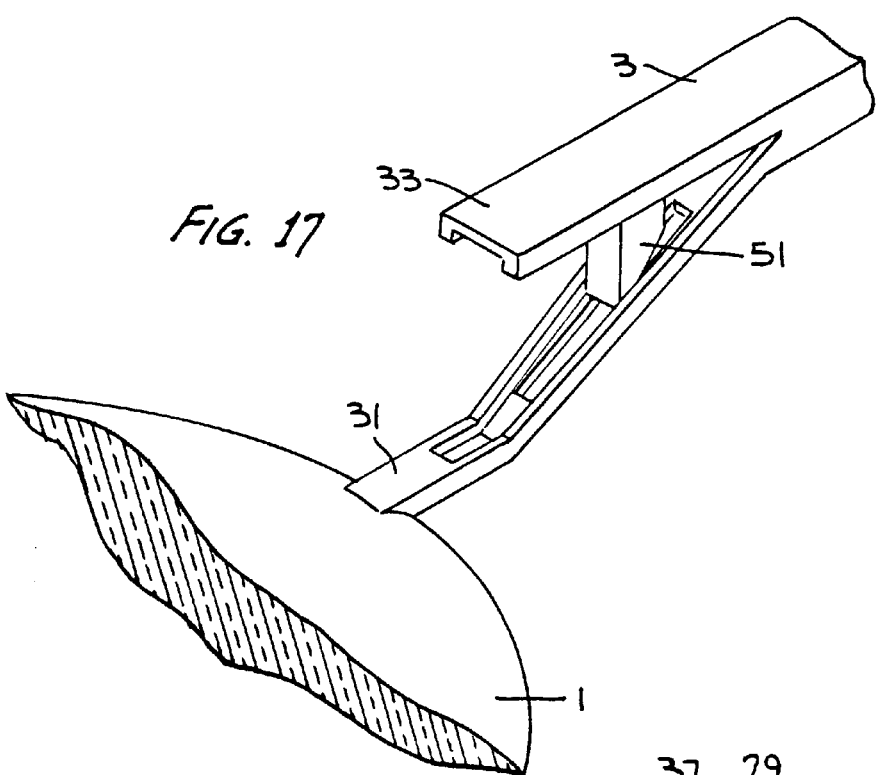
FIG. 17 shows a plan view of one of the fork ends from FIG. 16.

In the intraocular lens according to the invention in FIG. 16, at least one of the fork ends 31, 33 has, on the side facing towards the other fork end 33, 31, a toothing 49, similar to a toothed rack, where a spacer element 51 can be moved along the fork ends 31, 33 and can be fixed in position by engagement in the toothing. FIG. 17 shows a plan view of the outwardly directed fork end 31. The latter is preferably provided with a cental longitudinal slit through which access to the spacer element is possible.

Further adjustable intraocular lenses are shown in FIGS. 10 and 11. Here, the adjusting screw 37, the threaded hole 35 and the through-hole 43 are inclined relative to the optic axis 27. In this way, the point of intervention on the cornea, for post-operative adjustment, moves outwards and away from the patient's field of vision.

Figure 18:
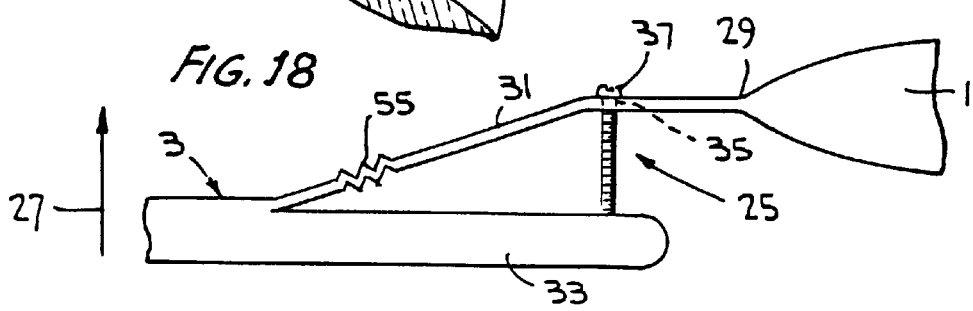
FIG. 18 shows a side view of a further lens according to the invention.

FIG. 18 shows a further lens according to the invention. This differs from the lens in FIGS. 6a and 6b in that an extension element 55 is provided in the fork end 31 between the threaded hole 35 and the bifurcation point, in order to better take up the change in length of the fork end 31. Such an extension element can also be provided at suitable points in the other embodiments of the invention. In FIG. 18, the extension element is an accordion-shaped section in the fork end 31.

Although a number of preferred embodiments have been set out in the above description, the invention is not limited thereto. Changes and modifications within the scope of the skilled person are also encompassed.

What is claimed is:

1. Adjustable intraocular lens comprising a lens body, haptic arms for fixing the lens body in an eye, and an adjustment means for moving the lens body repeatedly and reversibly in a direction of an optic axis of the lens body, wherein the haptic arms are each connected to the lens body at one end of each of the arms and the adjustment means is part of at least one of the haptic arms.

2. Adjustable intraocular lens according to claim 1 wherein the lens body is foldable or rollable.

3. Adjustable intraocular lens according to claim 1 wherein the adjustment means is constructed and arranged as an adjustable step in at least one of the haptic arms.

4. Adjustable intraocular lens comprising a lens body, haptic arms for fixing the lens body in an eye, and an adjustment means for moving the lens body repeatedly and reversibly in a direction of an optic axis of the lens body, wherein the haptic arms are each connected to the lens body at one end of each of the arms, the haptic arms have at one end, two deformable fork ends perpendicular to the optic axis, and the lens body is connected to only one of the two fork ends, and the adjustment means adjusts distance as present between the fork ends.

5. Adjustable intraocular lens according to claim 4 wherein the adjustment means comprises a threaded hole running in the direction of the optic axis through one of the two fork ends, and an adjusting screw which is screwable into the threaded hole so that the adjusting screw bears at one end against one of the fork ends.

6. Adjustable intraocular lens comprising a lens body, haptic arms for fixing the lens body in an eye, and an adjustment means for moving the lens body repeatedly and reversibly in a direction of an optic axis of the lens body, wherein the haptic arms are each connected to the lens body at one end of each of the arms and the adjustment means has a piezoelectric element which serves to move the adjustment means.

7. Adjustable intraocular lens according to claim 1 wherein the haptic arms are divided into two sections connected via the adjustment means which adjusts relative positioning of the two sections of the haptic arms in the direction of the optic axis.

8. Adjustable intraocular lens according to claim 7 wherein the adjustment means includes a pin which extends in the direction of the optic axis and which is connected to one of the two sections of the haptic arms while another section of the two sections is mounted so as to move along the pin.

9. Adjustable intraocular lens according to claim 8 wherein the adjustment means further comprises horseshoe-shaped spacers which are pushable tightly onto the pin between the two sections and which fix the distance between the two sections.

10. Adjustable intraocular lens according to claim 1 wherein at least one of the haptic arms has an extension element.

11. Adjustable intraocular lens according to claim 1 wherein one section of each of the haptic arms has, at one end, a cylindrical or disc-shaped end-piece which is aligned with the optic axis, and a second section of each of the haptic arms has at one end, a hollow cylindrical or flange-like end-piece which encloses the disc-shaped end-piece and holds the disc-shaped end-piece such that the disc-shaped end-piece can be moved axially.

12. Method of producing an intraocular lens having a lens body, haptic arms for fixing the lens body in an eye which are each connected to the lens body at one end of each of the arms, and an adjustment means for moving the lens body repeatedly and reversibly in a direction of an optic axis of the lens body comprising:

producing the lens body with the haptic arms attached thereto, forming a bifurcation in the haptic arms, and forming a threaded hole in at least one bifurcation of the haptic arms.

13. Method according to claim 12 wherein the haptic arms and the lens body are cast in one casting procedure.

14. Method according to claim 12 wherein each bifurcation and internal thread of the threaded hole are formed simultaneously by casting.

15. Adjustable intraocular lens comprising a lens body, haptic arms for fixing the lens body in an eye, and an adjustment means for moving the lens body relative to the haptic arms in a direction of an optic axis of the lens body, wherein the adjustment means includes a through-hole at an edge of the lens body into which through-hole an end-piece of at least one haptic arm of said haptic arms engages such that said at least one haptic arm can move axially.

\* \* \* \* \*